US008268885B2

(12) United States Patent
Van Acker et al.

(10) Patent No.: US 8,268,885 B2
(45) Date of Patent: Sep. 18, 2012

(54) ENTRY INHIBITORS OF THE HIV VIRUS

(75) Inventors: Koenraad Lodewijk August Van Acker, Temse (BE); Piet Tom Bert Paul Wigerinck, Terhagen (BE); Lieve Emma Jan Michiels, Mol (BE); Abdellah Tahri, Anderlecht (BE)

(73) Assignee: Janssen R&D Ireland, Cork (IE)

( * ) Notice: Subject to any disclaimer, the term of this patent is extended or adjusted under 35 U.S.C. 154(b) by 1895 days.

(21) Appl. No.: 10/571,325

(22) PCT Filed: Sep. 10, 2004

(86) PCT No.: PCT/EP2004/052139
§ 371 (c)(1),
(2), (4) Date: Mar. 8, 2006

(87) PCT Pub. No.: WO2005/023242
PCT Pub. Date: Mar. 17, 2005

(65) Prior Publication Data
US 2007/0066623 A1    Mar. 22, 2007

Related U.S. Application Data

(60) Provisional application No. 60/502,476, filed on Sep. 12, 2003.

(30) Foreign Application Priority Data

Sep. 11, 2003  (EP) .................................. 03103362

(51) Int. Cl.
| A61K 31/24 | (2006.01) |
| A61K 31/22 | (2006.01) |
| A61K 31/18 | (2006.01) |
| A61K 31/16 | (2006.01) |
| C07C 311/25 | (2006.01) |
| C07C 67/02 | (2006.01) |
| C07C 235/74 | (2006.01) |
| C07C 235/78 | (2006.01) |

(52) U.S. Cl. ........ 514/539; 514/549; 514/604; 514/616; 560/13; 560/255; 562/430; 564/82; 564/89; 564/91; 564/158

(58) Field of Classification Search .................. 514/539, 514/549, 604, 616; 560/13, 255; 564/91, 564/82, 89, 158; 562/430
See application file for complete search history.

(56) References Cited

U.S. PATENT DOCUMENTS 5,070,096 A    12/1991   Mohrs et al.
6,262,112 B1   7/2001    Mittendorf et al.

FOREIGN PATENT DOCUMENTS

| EP | 0721331 B1 | 7/1996 |
| EP | 0499299 B1 | 8/2000 |
| WO | WO 94/05263 A1 | 3/1994 |
| WO | WO 97/44014 A1 | 11/1997 |
| WO | WO 98/42318 A1 | 10/1998 |
| WO | WO 03/075907 A1 | 9/2003 |

OTHER PUBLICATIONS

Testa et al., "Predicting drug metabolism: Concepts and challenges", Pure Appl. Chem., vol. 76, No. 5, pp. 907-914, 2004.*
International Search Report, International Patent Application No. PCT/EP2004/052139, Date of Mailing of International Search Report Dec. 30, 2004.
Chen, J. et al, "Preparation of Aryloxyacetanilides Through Liquid-Liquid Phase Transfer Catalysis.", Yingyong Huaxue, 1989, vol. 6, No. 5, pp. 51-55, Database Chemabs. Chemical Abstracts Service, Columbus, Ohio, US, XP002269088. ((Chemical Abstract only provided).
Cross L.C., et al., "Rules for the Nomenclature of Organic Chemistry, Section E: Sterochemistry.", Pure & Appl. Chem., 1976, vol. 45, pp. 11-30.
Goodman and Gilman (The Pharmacological Basis of Therapeutics, 8th ed.), McGraw-Hill, Int. Ed. 1992, "Biotransformation of Drugs", pp. 13-15.
Greene T. W., et al., "Protective Groups in Organic Synthesis", $2^{nd}$ edition, T W Greene & P G M Wutz, Wiley Interscience, 1991.
Hertogs K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs.", Antimicrob Agents and Chemotherapy, Feb. 1998, vol. 42, No. 2, pp. 269-276.
Meanwell, N.A. et al., "Inhibitors of the Entry of HIV Into Host Cells.", Current Opinion in Drug Discovery and Development, Jul. 2003, vol. 6, No. 4, pp. 451-461, Current Drugs, London, GB, XP008021702.
Moore, J. et al., "Regularly Alternating Copoly(Amide-Enaminonitriles).", Macromolecules, Jun. 16, 1997, vol. 30, No. 12, American Chemical Society, Easton, US, XP000700737.
"Protective Groups in Organic Chemistry", edited by J W F McOmie, 1973, Plenum Press.
Redshaw, S. et all, "Fusion/Entry Inhibitors as Therapies for HIV.", Expert Opinion on Emerging Drugs, 2001, vol. 6, No. 2, pp. 209-224, XP002269087.

* cited by examiner

Primary Examiner — Peter G O Sullivan
(74) Attorney, Agent, or Firm — Toni-Junell Herbert

(57) ABSTRACT

The present invention relates to small molecules as entry inhibitors of the HIV virus, processes for their preparation as well as pharmaceutical compositions, their use as medicines, and diagnostic kits comprising them. The present invention also concerns combinations of the present entry inhibitors with other anti-retroviral agents. It further relates to their use in assays as reference compounds or as reagents. The compounds of the present invention are useful for preventing or treating infection by HIV and for treating AIDS.

1 Claim, No Drawings

ENTRY INHIBITORS OF THE HIV VIRUS

CROSS REFERENCE TO RELATED APPLICATIONS

This application is the national stage of PCT Application No. PCT/EP2004/052139, filed 10 Sep. 2004, which application claims priority from EP Patent Application No. 03103362.4, filed 11 Sep. 2003, and U.S. Patent Application No. 60/502,476, filed 12 Sep. 2003.

The present invention relates to small molecules as entry inhibitors of the HIV virus, processes for their preparation as well as pharmaceutical compositions, their use as medicines, and diagnostic kits comprising them. The present invention also concerns combinations of the present entry inhibitors with other anti-retroviral agents. It further relates to their use in assays as reference compounds or as reagents. The compounds of the present invention are useful for preventing or treating infection by HIV and for treating AIDS.

The number of people living with HIV/AIDS totaled in December 2001 about 40 million of which more than 37 million adults and about 2.7 million children under 15 years old. The people newly infected with HIV in 2001 alone rose to 5 million whereas there were in 2001 3 million AIDS deaths. Current chemotherapy for these people infected with HIV/AIDS employs the inhibitors of the viral fusion as well as reverse transcriptase (RT) and protease enzymes. In view of the emergence of HIV strains resistant to the current generation of RT and protease inhibitors, there exists an increasing need for the development of new antivirals with novel mechanisms of action.

One of the new areas of emerging antiretrovirals is the area of the small molecule entry inhibitors. These drugs are designed to block HIV from entering the human cell by interfering with various phases of attachment and fusion between HIV and the cell. The entry process can be divided in three sequentially distinct steps (1) binding of the virus envelope protein gp120 to the CD4 receptor on the host cell, (2) binding of the virus envelope protein gp120 to the co-receptors (CXCR4/CCR5) on the host cell, and (3) fusion of the virus and the host cell membranes, mediated by the virus envelope protein gp41.

Several (co)receptor inhibitors and two fusion inhibitors, T20 and T1249 (Trimeris, Durham, N.C., USA), peptides based on elements of gp41, are currently on the market or in the final stages of clinical development. The successful proof-of-principle studies conducted with T20 made that HIV fusion has been validated as a clinically relevant target.

However, the use of peptides has many drawbacks when they are to be developed as pharmaceutically acceptable drugs. Therefore, there is a need to develop small molecules which may block HIV from entering the human cell by interfering with various phases of attachment and fusion between HIV and the cell.

The compounds of the present invention having the formula (I),

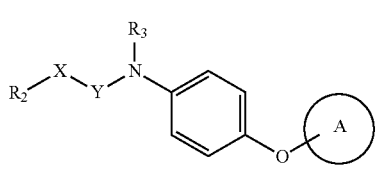

their N-oxide forms, stereochemical isomers, racemic mixtures, salts, prodrugs, esters and metabolites thereof, wherein A represents quinolinyl, isoquinolinyl, phenyl substituted with $R^1$, or 1,2,3,4-tetrahydroquinolinyl substituted with —Y—X—$R^2$;

X represents a direct bond, —$(CH_2)_t$—, —$(CH_2)_t$—NH—, —$(CH_2)_t$—NH—$(CH_2)_p$—, —$(CH_2)_t$—O— or —$(CH_2)_t$—O—$(CH_2)_p$—, and
if X is different from a direct bond, then X is connected to Y via a $CH_2$ group; and
each $CH_2$ group within the definition of X may optionally be substituted with —C(=O)—OH or —C(=O)—O—$C_{1-4}$alkyl, and Y represents —S(=O)$_2$— or —C(=O)—;
each t independently is an integer selected from 1, 2 or 3;
each p independently is an integer selected from 1, 2 or 3;
n independently is an integer selected from 0, 1 or 2;
$R^1$ represents —$NR^3$—Y—X—$R^2$, —$C_{1-4}$alkanediyl-$NR^3$—Y—X—$R^2$, —$NR^3$—Y—X—C(=O)—$C_{1-6}$alkyl or —$C_{1-4}$alkanediyl-$NR^3$—Y—X—C(=O)—$C_{1-6}$alkyl;
$R^2$ represents $C_{1-4}$alkyl, pyrrolidinyl optionally substituted with $C_{1-4}$alkyl, furanyl optionally substituted with $C_{1-4}$alkyl, piperazinyl optionally substituted with $C_{1-4}$alkyl, piperidinyl optionally substituted with $C_{1-4}$alkyl, thienyl optionally substituted with $C_{1-4}$alkyl, benzo-1,3-dioxolanyl, or phenyl optionally substituted with one or more substituents selected from the group consisting of $C_{1-6}$alkyl, $C_{1-6}$alkyloxy, hydroxy, carboxyl, $C_{1-6}$alkyloxycarbonyl, cyano, nitro, halogen, trifluoromethyl, amino, mono- or di($C_{1-6}$alkyl)amino, $C_{1-6}$alkylcarbonylamino, $C_{1-6}$alkylcarbonyl, mono- or di($C_{1-6}$alkyl)aminocarbonyl and aminocarbonyl;
$R^3$ represents hydrogen, $C_{1-6}$alkyl or $C_{3-7}$cycloalkyl;

are useful in the treatment of individuals infected by HIV and for the prophylaxis of these individuals.

In general, the compounds of formula (I) may be useful in the treatment of warm-blooded animals infected with viruses whose existence is mediated by, or depends upon, fusion of HIV with a human cell. Conditions associated with HIV which may be prevented or treated with the compounds of the present invention include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV, in particular HIV-1. Consequently, the compounds of the present invention can be used in the manufacture of a medicament useful for treating conditions associated with HIV.

In a preferred embodiment, the invention relates to the use of the compounds of the present invention or any subgroup thereof in the manufacture of a medicament for treating or combating infection or disease associated with HIV infection in a mammal. Thus, the invention also relates to a method of treating a HIV infection, or a disease associated with HIV infection comprising administering to a mammal in need thereof an effective amount of the compounds of formula (I) or a subgroup thereof.

In another preferred embodiment, the present invention relates to the use of the compounds or any subgroup thereof in the manufacture of a medicament for inhibiting entry of HIV in a mammal infected with said HIV, in particular HIV-1 retrovirus.

In another preferred embodiment, the present invention relates to the use of the compounds or any subgroup thereof in the manufacture of a medicament for inhibiting HIV entry, in particular for blocking HIV from entering the human cell by interfering with various phases of attachment and fusion between HIV and the cell.

Also, the present invention concerns the use of the compounds of formula (I) for the manufacture of a medicament useful for preventing HIV transmission or infection in humans, in particular transmission via sexual intercourse or related intimate contact between partners.

Thus, the present invention concerns a method of treating conditions associated with HIV infection, such as AIDS, AIDS related complex, progressive generalized lymphadenopathy (PGL), as well as chronic CNS diseases caused by HIV, such as, for example HIV mediated dementia and multiple sclerosis, in a subject in need thereof, in particular a human being, comprising administering to such subject an effective amount of a compound of formula (I).

The present invention also concerns a method for blocking HIV from entering a mammalian cell by interfering with various phases of attachment and fusion between HIV and the cell, in a subject in need thereof, in particular a human cell in a human being, comprising administering to such subject an effective amount of a compound of formula (I).

The present invention also concerns a method of preventing HIV transmission or infection in a subject in need thereof, in particular a human being, comprising administering to such subject an effective amount of a compound of formula (I).

Several subgroups of the compounds of formula (I) are deemed to be novel, and thus the present invention also concerns novel compounds. For instance, the compounds which are exemplified in the experimental part are deemed to be novel.

This invention also concerns the quaternization of the nitrogen atoms of the present compounds. A basic nitrogen can be quaternized with any agent known to those of ordinary skill in the art including, for instance, lower alkyl halides, dialkyl sulfates, long chain halides and arylalkyl halides.

As used herein, the term "halo" or "halogen" as a group or part of a group is generic for fluoro, chloro, bromo or iodo.

The term $C_{1-4}$alkyl, alone or in combination, means straight and branched chained saturated hydrocarbon radicals containing from 1 to 4 carbon atoms. Examples of such $C_{1-4}$alkyl radicals include methyl, ethyl, n-propyl, isopropyl, n-butyl, isobutyl, sec-butyl, tert-butyl and the like.

The term $C_{1-6}$alkyl, alone or in combination, means straight and branched chained saturated hydrocarbon radicals containing from 1 to 6 carbon atoms. Examples of such $C_{1-6}$alkyl radicals include methyl, ethyl, n-propyl, isopropyl, n-butyl, isobutyl, sec-butyl, tert-butyl, 2-methylbutyl, pentyl, iso-amyl, hexyl, 3-methylpentyl and the like.

The term $C_{1-6}$alkanediyl, alone or in combination, defines bivalent straight and branched chained saturated hydrocarbon radicals containing from 1 to 6 carbon atoms, such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term $C_{3-7}$cycloalkyl as a group or part of a group is generic to cyclopropyl, cyclobutyl, cyclopentyl, cyclohexyl and cycloheptyl.

As used herein, the term $C(=O)$ is meant to define a carbonyl moiety, the term $C(=S)$ is meant to define a thiocarbonyl moiety, the term $S(=O)$ is meant to define a sulfoxyl or sulfinyl moiety, the term $S(=O)_2$ is meant to define a sulfonyl moiety, the term $C(=NH)$ is meant to define an imino moiety and the term $C(=NCN)$ is meant to define a cyanoimino moiety.

As used herein, the term hydroxy means —OH, the term nitro means —NO$_2$, the term cyano means —CN, the term thio means —S, the term oxo means =O.

Whenever the terms "one or more substituents" or "substituted" are used in defining the compounds of formula (I), it is meant to indicate that one or more hydrogens on the atom indicated in the expressions using "one or more substituents" or "substituted' is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

The term "prodrug" as used throughout this text means the pharmacologically acceptable derivatives such as esters, amides and phosphates, such that the resulting in vivo biotransformation product of the derivative is the active drug as defined in the compounds of the present invention. The reference by Goodman and Gilman (The Pharmacological Basis of Therapeutics, 8$^{th}$ ed, McGraw-Hill, Int. Ed. 1992, "Biotransformation of Drugs", pp 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, or an amino group is bonded to any group that, when the prodrug is administered to a patient, cleaves to form a free hydroxyl or free amino, respectively.

Prodrugs are characterized by excellent aqueous solubility, increased bioavailability and are readily metabolized into the active inhibitors in vivo.

For therapeutic use, the salts of the compounds of the present invention are those wherein the counter-ion is pharmaceutically or physiologically acceptable. However, salts having a pharmaceutically unacceptable counter-ion may also find use, for example, in the preparation or purification of a pharmaceutically acceptable compound of the present invention. All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of the present invention containing an acidic proton may also be converted into their non-toxic metal or amine addition salt form by treatment with appropriate organic and inorganic bases. Appropriate base salt forms comprise, for example, the ammonium salts, quaternary ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

The N-oxide forms of the present compounds are meant to comprise the compounds wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess and the diastereomeric excess respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of the present invention can be obtained separately by conventional methods. Appropriate physical separation methods which may advantageously be employed are, for example, selective crystallization and chromatography, e.g. column chromatography.

The compounds may contain one or more asymmetric centers and thus may exist as different stereoisomeric forms. The absolute configuration of each asymmetric center that may be present in the compounds may be indicated by the stereochemical descriptors R and S, this R and S notation corresponding to the rules described in Pure Appl. Chem. 1976, 45, 11-30.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The favourable properties of the present compounds with respect to their ability to block the fusion process between HIV and a human cell can be demonstrated using (i) an anti-viral replication assay that directly measures the ongoing replication of virus in MT4 cells via the specific interaction of HIV-tat with LTR sequences coupled to GFP (MT4-LTR-EGFP cells), or (ii) an entry reporter assay (ERA) that measures inhibition of cell-cell fusion between cell line persistently expressing HIV (effector cell line) and a cell line expressing CD4 and CXCR4 (target cell line) equipped with LTR-EGFP using FACS read-out.

A toxicity assay wherein a reduced expression of the GFP reporter protein (Mt4-CMV-EGFP cells) serves as a marker for cellular toxicity of a test compound can be used to measure the toxicity of the present compounds.

Compounds of formula (I) wherein A is a phenyl ring and $R^1$ is linked to the phenyl ring via a nitrogen atom, said $R^1$ being represented by —$NR^3$—$R^{1a}$ and said compounds of formula (I) being represented by formula (I-1) can be prepared according to scheme 1.

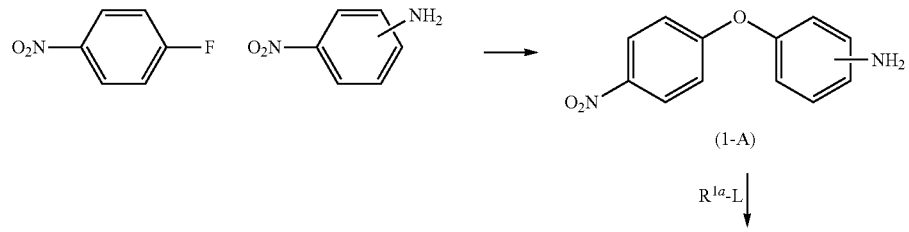

Scheme 1

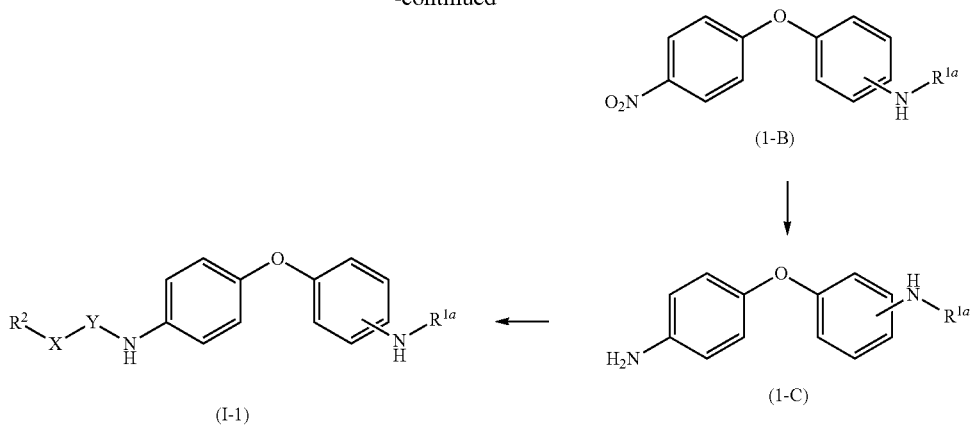

(1-B)

(1-C)

(I-1)

In the first step of scheme 1, aminophenol can be reacted with para-fluoronitrobenzene in the presence of a base, such as potassium carbonate, in a reaction inert solvent such as N,N-dimethylformamide to prepare an intermediate of formula (1-A). Subsequently, intermediate (1-A) can be reacted with an intermediate of formula $R^{1a}$—L wherein L is a suitable leaving group such as a halogen, in the presence of a base, such as potassium carbonate, in a solvent such as tetrahydrofuran and water to form an intermediate of formula (1-B). The nitro group in said intermediate (1-B) can be reduced to an amino group using art-known reduction techniques like a catalytic amount of palladium on carbon, optionally poisoned with thiophene, in a solvent like methanol, thus preparing an intermediate of formula (1-C). This intermediate of formula (1-C) can then further be reacted to a compound of formula (I-1) by reacting it with an intermediate of formula $R^2$—X—Y-L wherein L is a suitable leaving group such as for example a halogen, in the presence of a base such as potassium carbonate in a solvent such as tetrahydrofuran and water.

It should be noted that compounds of formula (I-1) wherein $R^3$ is other than hydrogen can be derived from the compounds of formula (I-1) wherein $R^3$ is hydrogen using art-known transformation techniques. Also, during the reduction step of the nitro group in intermediate (1-B), some reactive groups in the definition of $R^1$ may conveniently be protected with a suitable protecting group.

Scheme 2

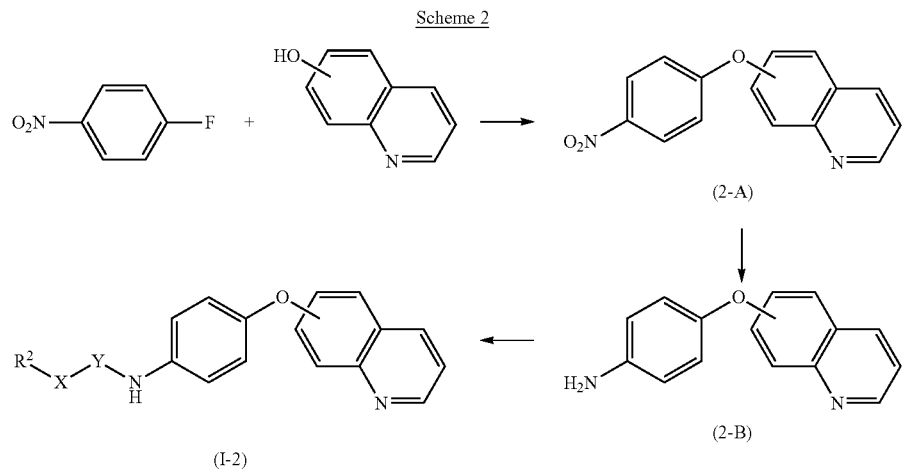

(2-A)

(2-B)

(I-2)

Scheme 2 shows a general procedure to prepare compounds of formula (I) wherein A is a quinolinyl group said compounds of formula (I) being represented by formula (I-2). The first step is similar to the one of scheme 1 and involves a reaction in the presence of a base such as potassium carbonate in a reaction-inert solvent such as N,N-dimethylformamide to prepare an intermediate of formula (2-A). The nitro moiety can be reduced to an amino group using art-known techniques to form intermediate (2-B) which in turn, like in scheme 1, can be further reacted with an intermediate of formula $R^2$—X—Y-L wherein L is a suitable leaving group, such as for example a halogen, in the presence of a base such as potassium carbonate in a solvent such as tetrahydrofuran and water.

Analogous to the preparation of compounds of formula (I-2) in scheme 2, compounds of formula (I) wherein A is isoquinolinyl, said compounds being represented by formula (I-3), can be prepared.

Compounds of formula (I) wherein A is 1,2,3,4-tetrahydroquinolinyl substituted with Y—X—$R^2$, said compounds being represented by formula (I-4), can be prepared according to scheme 4.

Scheme 4

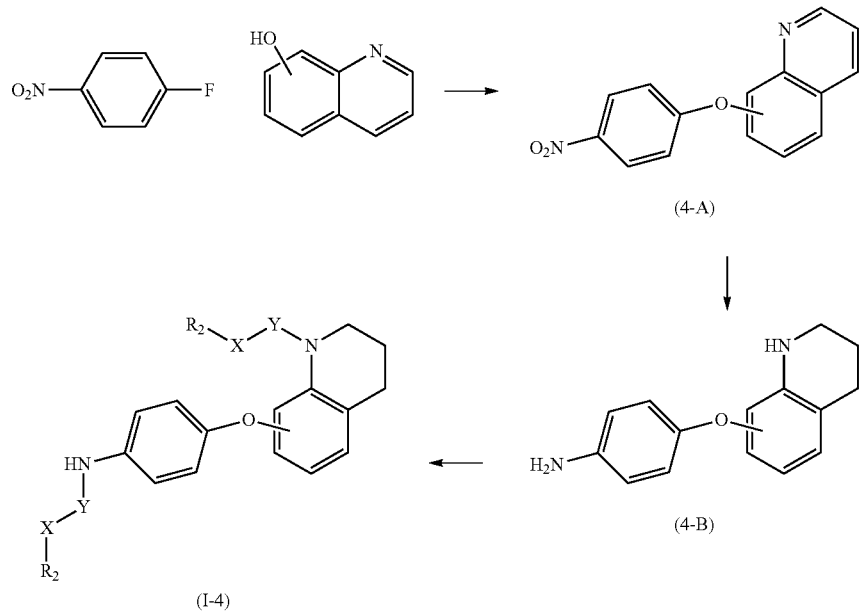

The preparation of intermediate (4-A) is analogous to the preparation of intermediate (2-A) in scheme 2. Intermediate (4-B) can be prepared by reducing intermediate (4-A) using art-known reduction techniques like a catalytic amount of palladium on carbon, optionally poisoned with thiophene, in a solvent like methanol. Starting from intermediate (4-B), compounds of formula (I-4) wherein the two —Y—X—$R^2$ moieties are identical can be prepared by reacting it with a reagent of formula $R^2$—X—Y—COCl or $R^2$—X—Y—$SO_2$—Cl in the presence of a base, such as potassium carbonate, in a solvent such as tetrahydrofuran and water.

Compounds of formula (I-4) wherein the two Y—X—$R^2$ groups are different can be prepared using the same basic procedure, but the reduction step to form intermediates of formula (4-B) is carried out selectively to reduce only one the nitro function or the ring nitrogen. For this purpose, art-known techniques such as poisoning the catalyst (palladium on carbon) with thiophene. Once the first Y—X—$R^2$ group is introduced the second functional nitrogen can then be reduced and further reacted with Y—X—$R^2$.

Compounds of formula (I) wherein A is a phenyl ring and $R^1$ is linked to the phenyl ring via a carbon atom, said $R^1$ being represented by —C—$R^{1b}$ and said compounds of formula (I) being represented by formula (I-5) can be prepared according to scheme 5.

Scheme 5

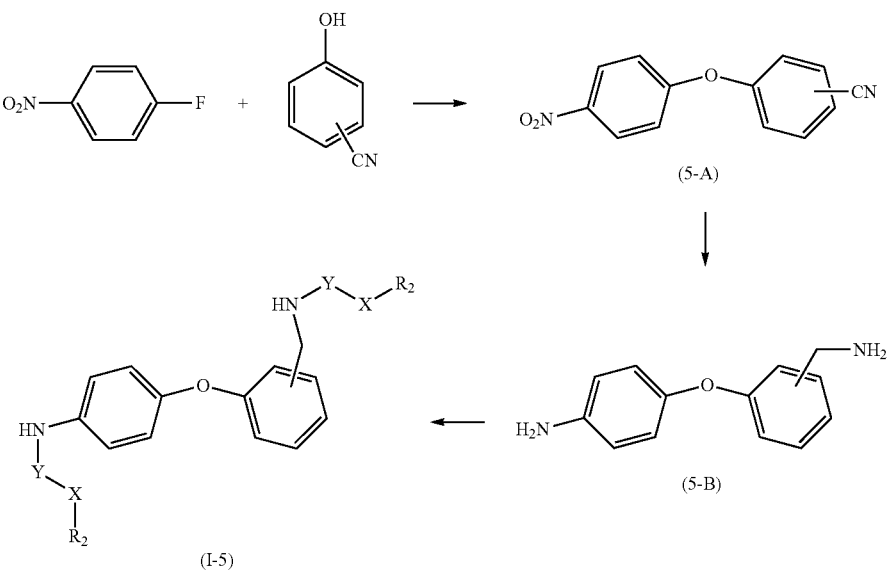

Intermediates of formula (5-A) can be prepared analogous the intermediates of formula (1-A) in scheme 1. In case the linker between $NR^3$—Y—X—$R^2$ and the phenyl ring in the compounds of formula (I-5) needs to be longer than 1 carbon atom, a suitably adapted cyanophenol can be used as starting material, for instance hydroxybenzeneacetonitrile or hydroxybenzenepropanenitrile and the like. The intermediate (5-A) can be reduced to an intermediate of formula (5-B) by using art-known reduction techniques such as palladium on carbon in a solvent such as methanol. Said intermediate of formula (5-B) can then be further reacted with a reagent of formula $R^2$—X—Y—COCl or $R^2$—X—Y—$SO_2$—Cl in the presence of a base, such as potassium carbonate, in a solvent such as tetrahydrofuran and water.

Like in scheme 4, compounds of formula (I-5) wherein the two Y—X—$R^2$ groups are different can be prepared using the same basic procedure, but with selective reduction of the cyano group and the nitro group.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

In preparations presented above, the reaction products may be isolated from the reaction medium and, if necessary, further purified according to methodologies generally known in the art such as, for example, extraction, crystallization, distillation, trituration and chromatography.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of the compound. The pharmaceutical preparations can be prepared in a manner known per se to one of skill in the art. For this purpose, at least one of a compound of the present invention, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4; fusion inhibitors, such as, for example, T20, T1249, SHC-C; co-receptor binding inhibitors, such as, for example, AMD 3100 (Bicyclams), TAK 779; RT inhibitors, such as, for example, foscarnet and prodrugs; nucleoside RTIs, such as, for example, AZT, 3TC, DDC, DDI, D4T, Abacavir, FTC, Emtricitabine, DAPD, dOTC; nucleotide RTIs, such as, for example, PMEA, PMPA, tenofovir; NNRTIs, such as, for example, nevirapine, delavirdine, efavirenz, 8 and 9-Cl TIBO (tivirapine), loviride, TMC-125, TMC-120, MKC-442, UC 781, Capravirine, DPC 961, DPC963, DPC082, DPC083, calanolide A, SJ-3366, TSAO, 4"-deaminated TSAO; RNAse H inhibitors, such as, for example, SP1093V, PD126338; TAT inhibitors, such as, for example, RO-5-3335, K12, K37; integrase inhibitors, such as, for example, L 708906, L 731988; protease inhibitors, such as, for example, amprenavir, ritonavir, nelfinavir, saquinavir, indinavir, lopinavir, lasinavir, BMS 232632, BMS 186316, DPC 681, DPC 684, tipranavir, AG1776, DMP 450, L 756425, PD178390, PNU 140135; glycosylation inhibitors, such as, for example, castanospermine, deoxynojirimycine.

The combination may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) or with antibiotics (e.g., pentamidine isothiorate) to ameliorate, combat, or eliminate HIV infection and its symptoms.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds in pharmaceutical compositions, it can be advantageous to employ $\alpha$-, $\beta$- or $\gamma$-cyclo-dextrins or their derivatives. Also co-solvents such as alcohols may improve the solubility and/or the stability of the compounds in pharmaceutical compositions. In the preparation of aqueous compositions, addition salts of the subject compounds are obviously more suitable due to their increased water solubility.

Appropriate cyclodextrins are $\alpha$-, $\beta$- or $\gamma$-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated $\beta$-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkyloxycarbonylalkyl or carboxy-alkyloxyalkyl, particularly carboxymethoxypropyl or carboxyethoxypropyl; alkylcarbonyloxyalkyl, particularly 2-acetyloxypropyl. Especially noteworthy as complexants and/or solubilizers are $\beta$-CD, randomly methylated $\beta$-CD, 2,6-dimethyl-$\beta$-CD, 2-hydroxyethyl-$\beta$-CD, 2-hydroxyethyl-$\gamma$-CD, 2-hydroxypropyl-$\gamma$-CD and (2-carboxymethoxy)propyl-$\beta$-CD, and in particular 2-hydroxypropyl-$\beta$-CD (2-HP-$\beta$-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, PCT application No. PCT/EP98/01773, EP-A-499299 and WO 97/44014, all incorporated herein by reference.

More in particular, the present compounds may be formulated in a pharmaceutical composition comprising a therapeutically effective amount of particles consisting of a solid dispersion comprising (a) a compound of the present invention, and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the compounds of this invention are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of the present invention, in an amount effective for use as a standard or reagent in a test or assay for determining the ability of a potential pharmaceutical to inhibit HIV entry, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. Antimicrob Agents Chemother, 1998; 42(2): 269-276, incorporated by reference).

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of the present invention, in the case of administration to a patient approximately 75 kg in weight is 1 mg to 1 g, preferably 3 mg to 0.5 g. The dose can be administered in the form of an individual dose, or divided into several, e.g. two, three, or four, individual doses.

EXPERIMENTAL PART

Preparation of compound 1 according to scheme A.
[acetic acid {4-[4-(4-methoxy-benzenesulfonylamino)-phenoxy]-phenylcarbamoyl}-methyl ester]

Scheme A

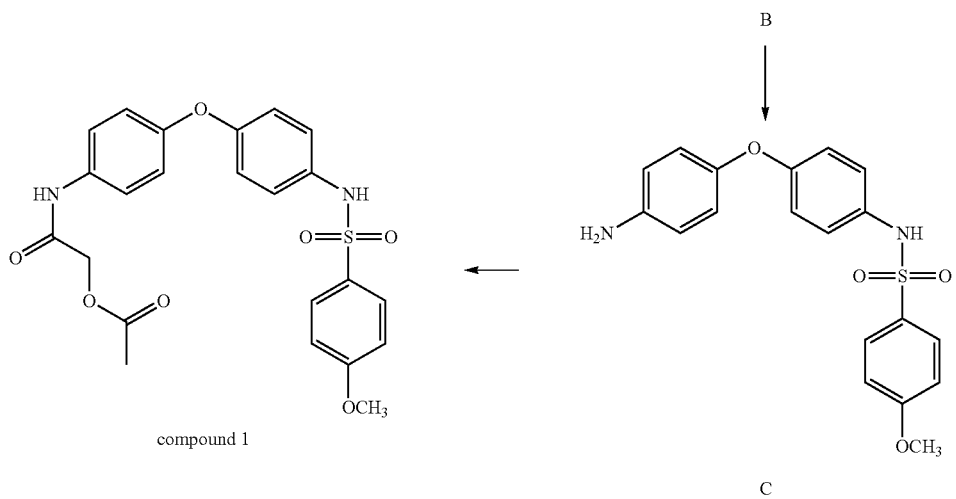

Preparation of Intermediate (A)

To a mixture of 20 g of amino phenol in 400 ml of N,N-dimethylformamide (DMF), at room temperature, was added potassium carbonate 30 g (1.2 equivalent). The mixture was stirred and the para-fluoronitrobenzen 25.8 g was added. The reaction mixture was stirred for 12 hours at room temperature. When starting material was consumed the mixture was then poured in water (250 ml). The solution was acidified by adding a solution of hydrochloric acid until pH=7. The DMF was evaporated and the product was extracted with ethyl acetate. The organic layer was separated, dried over $MgSO_4$ and evaporated to yield 30 g (71%) of intermediate A.

Preparation of Compounds of Formula B

To a mixture of 1 g of intermediate A in 25 ml of tetrahydrofurane (THF), at room temperature, was added water 15 ml and potassium carbonate 1.18 g (2 equivalents). The mixture was stirred and 988 mg of the para-methoxysulfonylchloride was added (1.1 equivalent). The reaction mixture was stirred for 4 hours at room temperature. The water (25 ml) was added and the product was extracted with ethyl acetate. The organic layer was separated, dried over MgSO4, and evaporated to yield 1.44 g (83%) of intermediate B.

Preparation of Intermediate C

A mixture of intermediate B 1.24 g was dissolved in methanol and a catalytic amount of palladium on carbon was added. The mixture was stirred at room temperature under hydrogen. After 4 hours the mixture was filtered and the solvent was removed. Intermediate C 700 mg (61%) was isolated.

Preparation of Compound 1

To a mixture of 500 mg of intermediate C in 10 ml of THF, at room temperature, was added water 10 ml and potassium carbonate 429 mg. The mixture was stirred and 203 mg of acetoxyacetyl chloride was added (1.1 equivalent). The reaction mixture was stirred for 4 hours at room temperature. The water (50 ml) was added and the product was extracted with (3×20 ml) ethyl acetate. The organic layer was separated, dried over $MgSO_4$, and evaporated to yield 377 mg (80%) of compound 1.

Preparation of compound 23 according to scheme B.
[Furan-2-carboxylic acid {4-[1-(furan-2-carbonyl)-1,2,3,4-tetrahydro-quinolin-8-yloxy]-phenyl}-amide]

Scheme B

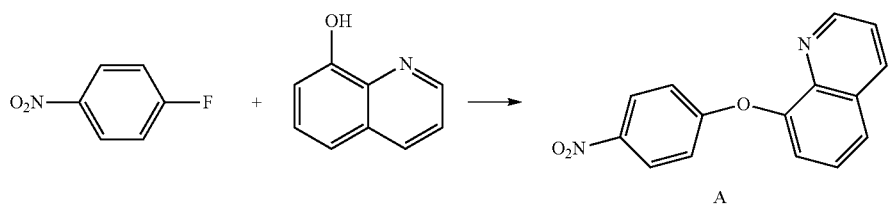

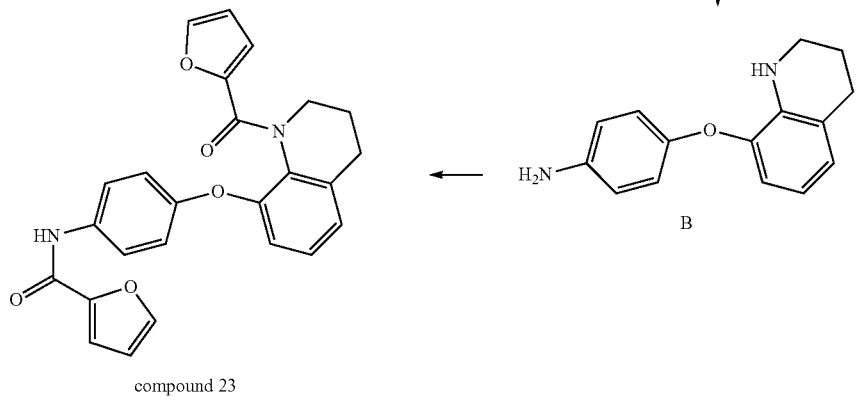

compound 23

Preparation of Intermediate A

To a mixture of 1 g of 8-hydroxy-quinoleine in 20 ml of DMF, at room temperature, was added potassium carbonate 2.85 g (1.1 equivalent). The mixture was stirred and the para-fluoronitrobenzen 1 g was added. The reaction mixture was stirred for 3 hours at 140° C. When starting material was consumed the mixture was than poured in water (25 ml). The solution was acidified by adding a solution of hydrochloric acid until pH=7. The DMF was removed and the product was extracted with ethyl acetate. The organic layer was separated, dried over $MgSO_4$ and evaporated to yield 1.5 g (81%) of intermediate A.

Preparation of Compound B

A mixture of intermediate A 1.5 g was dissolved in methanol and a catalytic amount of palladium on carbon was added. The mixture was stirred at room temperature under hydrogen. After 4 hours the mixture was filtered and the solvent was removed intermediate B 1.4 g (86%) was isolated.

Preparation of Compound 23

To a mixture of 200 mg of intermediate B in 10 ml of THF, at room temperature, was added water 10 ml and potassium carbonate 260 mg. The mixture was stirred and 2-furancarbonylchloride was added (2.2 equivalent). The reaction mixture was stirred for 12 hours at room temperature. The water (20 ml) was added and the product was extracted with (3×20 ml) ethyl acetate. The organic layer was separated, dried over $MgSO_4$, and evaporated to yield compound 23.

Preparation of compound 9 according to scheme C.
[N,N'-(oxydi-4,1-phenylene)-bis(2-furancarboxamide)]

Scheme C

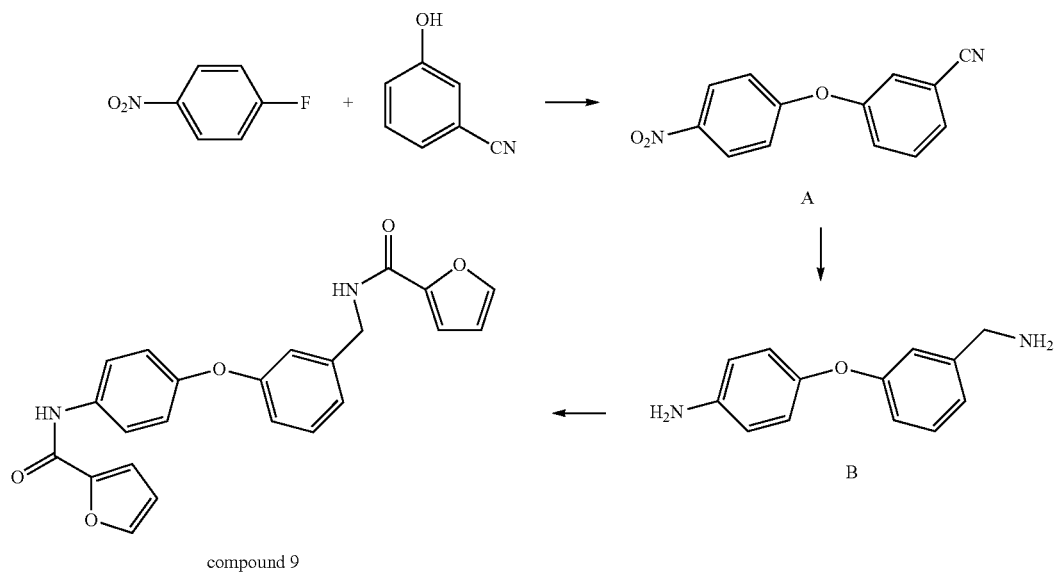

compound 9

Preparation of Intermediate A

To a mixture of 1 g of 3-cyanophenol in 20 ml of DMF, at room temperature, was added potassium carbonate 1.27 g (1.1 equivalent). The mixture was stirred and the para-fluoronitrobenzen 1 g was added. The reaction mixture was stirred for 3 hours at 140° C. When starting material was consumed the mixture was than poured in water (25 ml). The solution was acidified by adding a solution of hydrochloric acid until pH=7. The DMF was removed and the product was extracted with ethyl acetate. The organic layer was separated, dried over MgSO$_4$ and evaporated to yield 1.6 g (80%) of intermediate A.

Preparation of Intermediate B

A mixture of intermediate A 1.6 g was dissolved in methanol and a catalytic amount of palladium on carbon was added. The mixture was stirred at room temperature under hydrogen. After 4 hours the mixture was filtered and the solvent was removed. intermediate B 1.2 g (85%) was isolated.

Preparation of Compound 9

To a mixture of 300 mg of intermediate B in 10 ml of THF, at room temperature, was added water 10 ml and potassium carbonate 2.2 equivalents. The mixture was stirred and 2-furancarbonylchloride was added (2.2 equivalents). The reaction mixture was stirred for 12 hours at room temperature. The water (20 ml) was added and the product was extracted with (3×20 ml) of ethyl acetate. The organic layer was separated, dried over MgSO$_4$, and evaporated to yield compound 9.

The compounds listed in table 1 can be prepared analogous to any one of the described reaction schemes.

TABLE 1

| Co. No. | Structure |
|---|---|
| 1 | 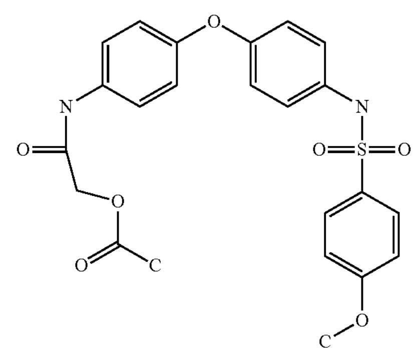 |
| 2 | 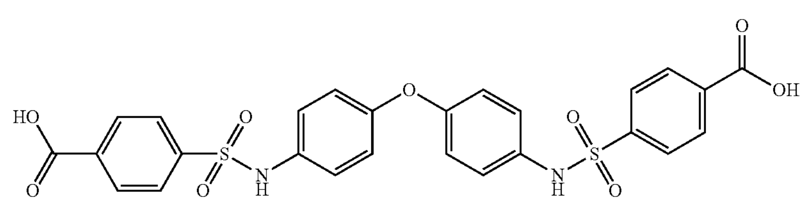 |
| 3 | 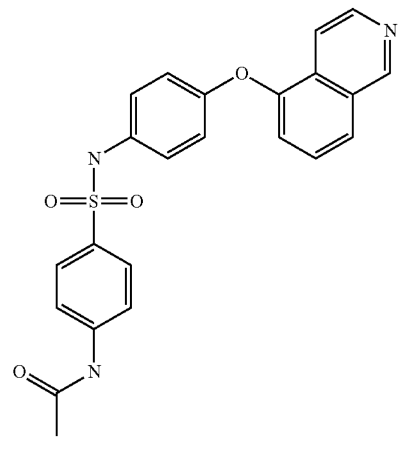 |

TABLE 1-continued

| Co. No. | Structure |
|---|---|
| 4 | 4-nitro-N-[4-(isoquinolin-5-yloxy)phenyl]benzamide |
| 5 | 4-cyano-N-[4-(isoquinolin-5-yloxy)phenyl]benzamide |
| 6 | 4-{[4-(isoquinolin-5-yloxy)phenyl]sulfamoyl}benzoic acid |
| 7 | 1-[2-(pyrrolidin-1-yl)ethylamino]acetyl-8-{4-[2-(pyrrolidin-1-yl)ethylamino]acetylamino-phenoxy}-1,2,3,4-tetrahydroquinoline |

TABLE 1-continued

| Co. No. | Structure |
|---|---|
| 8 | 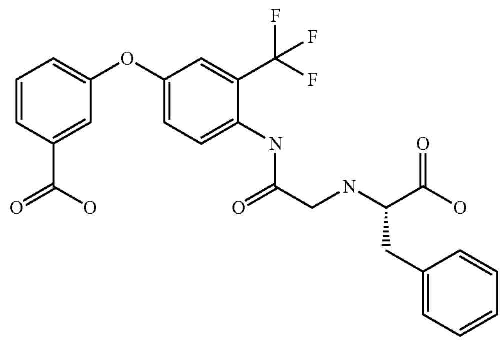 |
| 9 | 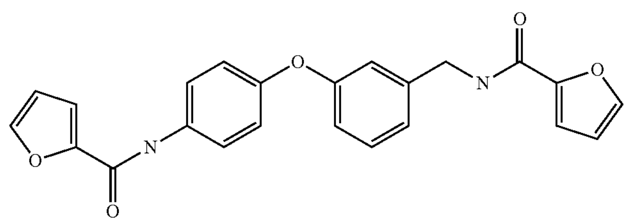 |
| 10 | 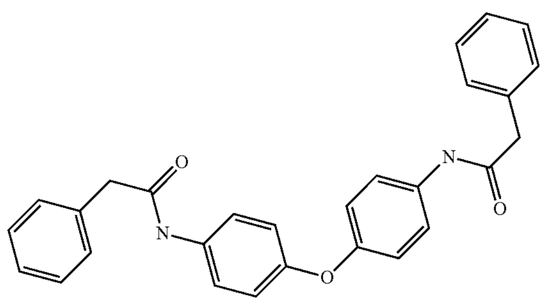 |
| 11 | 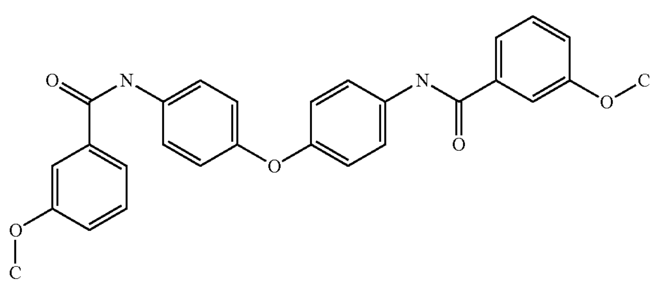 |
| 12 | 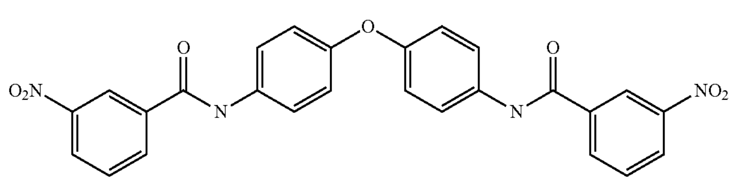 |
| 13 | 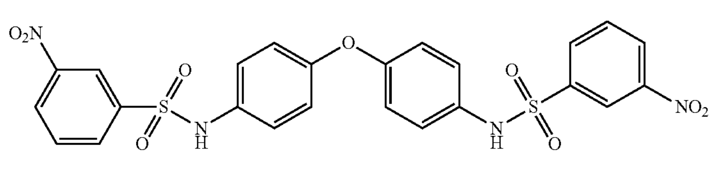 |

TABLE 1-continued

| Co. No. | Structure |
| --- | --- |
| 14 | 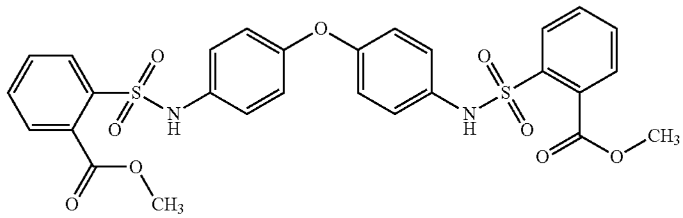 |
| 15 | 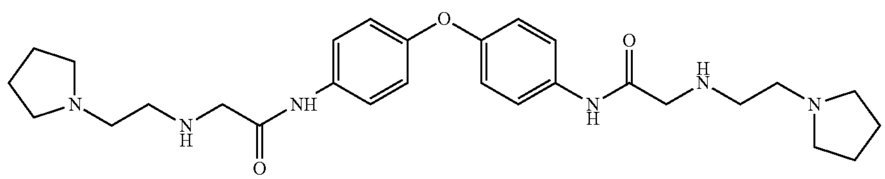 |
| 16 | 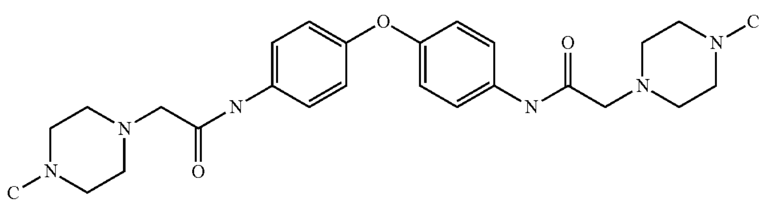 |
| 17 | 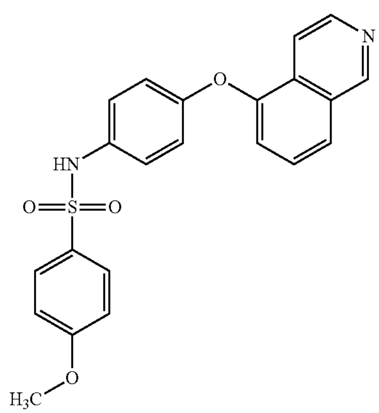 |
| 18 | 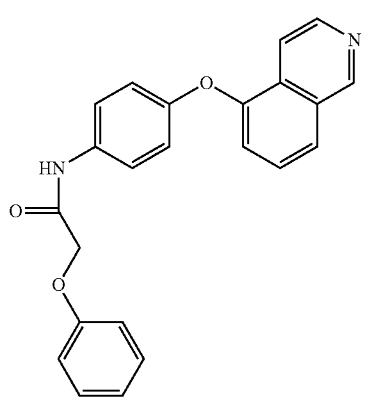 |

TABLE 1-continued
| Co. No. | Structure |
|---|---|
| 19 | 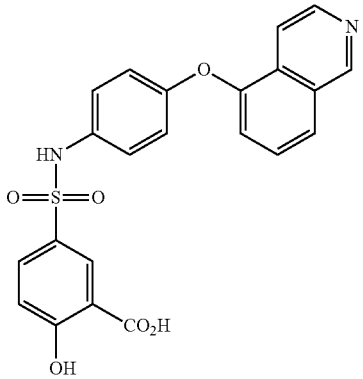 |
| 20 | 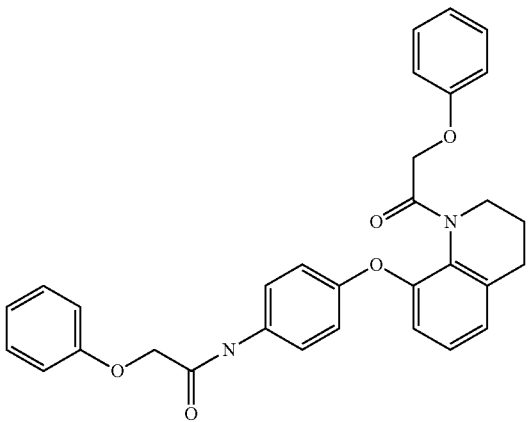 |
| 21 | 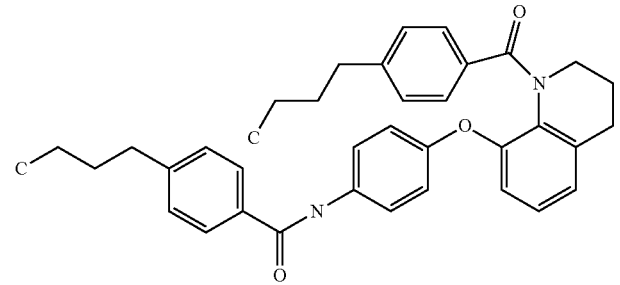 |
| 22 | 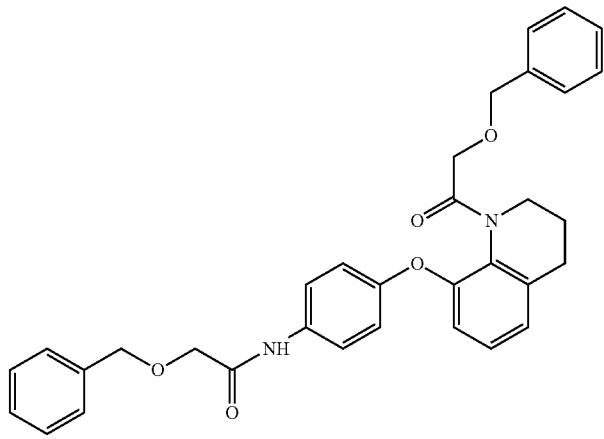 |

TABLE 1-continued

| Co. No. | Structure |
|---|---|
| 23 | 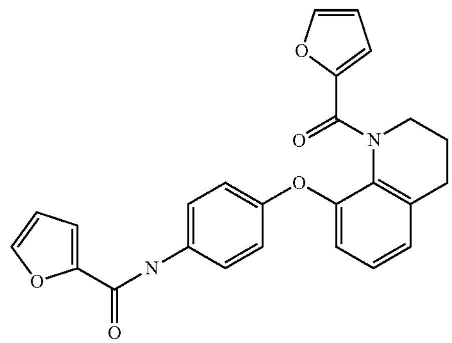 |
| 24 | 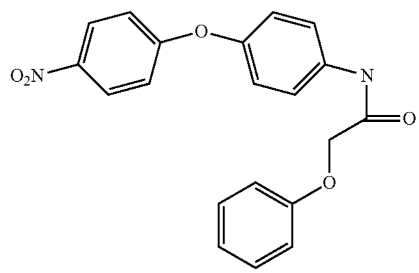 |
| 25 | 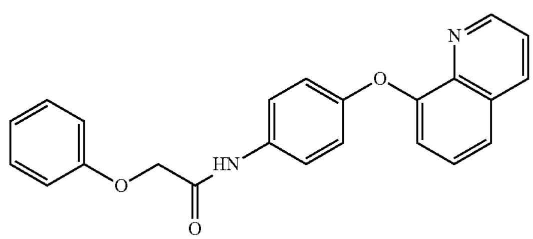 |
| 26 | 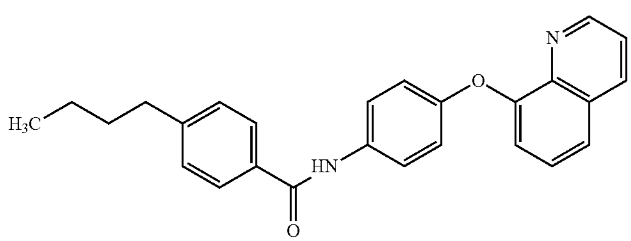 |
| 27 | 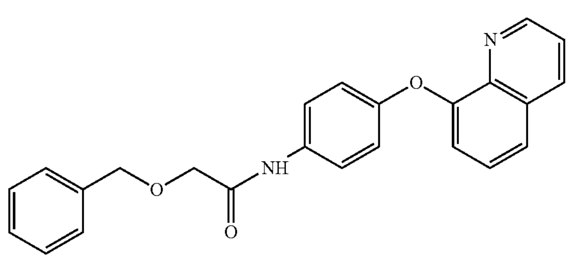 |
| 28 | 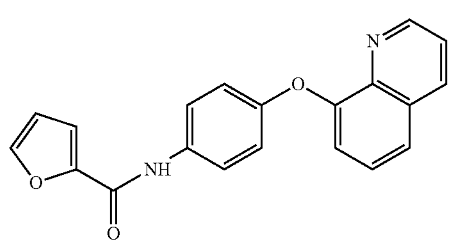 |

TABLE 1-continued

| Co. No. | Structure |
|---------|-----------|
| 29 | 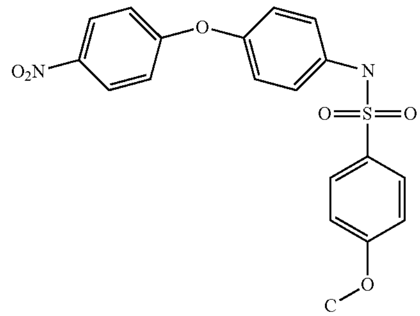 |
| 30 | 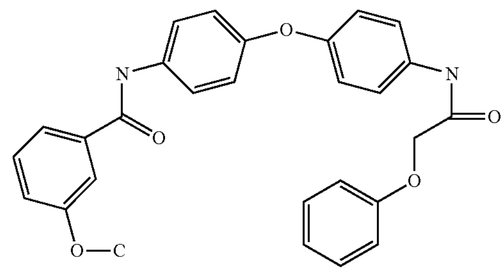 |
| 31 | 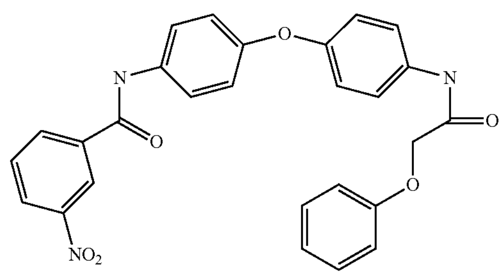 |
| 32 | 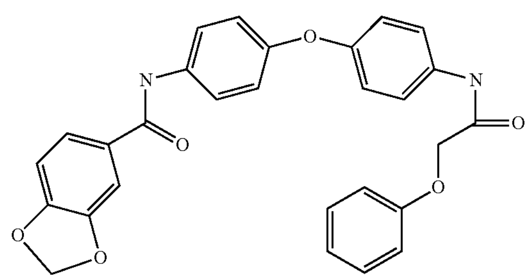 |
| 33 | 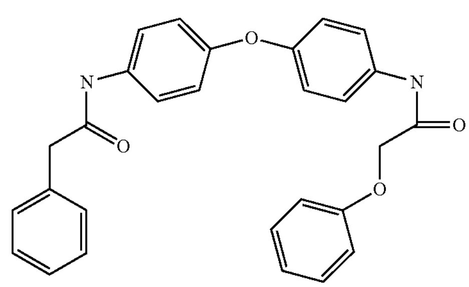 |

TABLE 1-continued

| Co. No. | Structure |
|---|---|
| 34 | 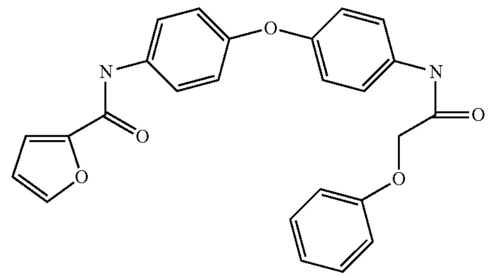 |
| 35 | 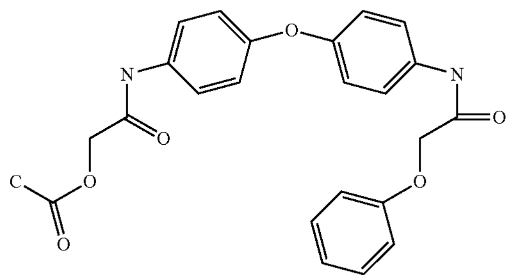 |
| 36 | 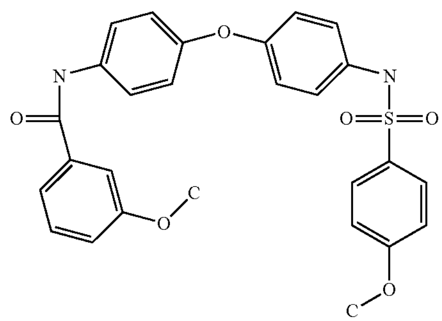 |
| 37 | 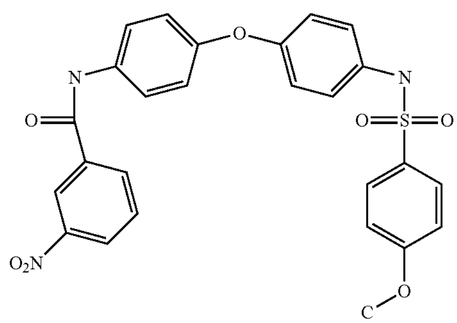 |
| 38 | 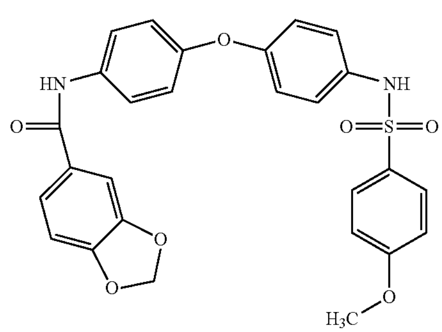 |

TABLE 1-continued
| Co. No. | Structure |
|---|---|
| 39 | 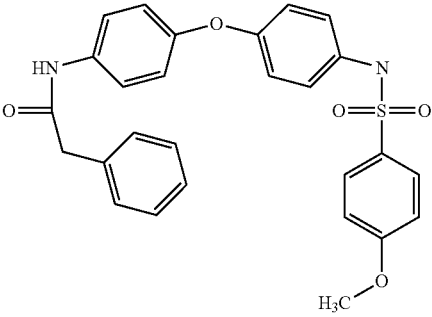 |
| 40 | 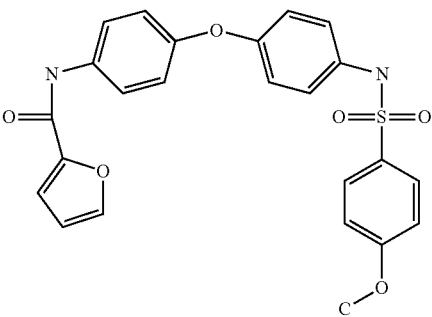 |
| 41 | 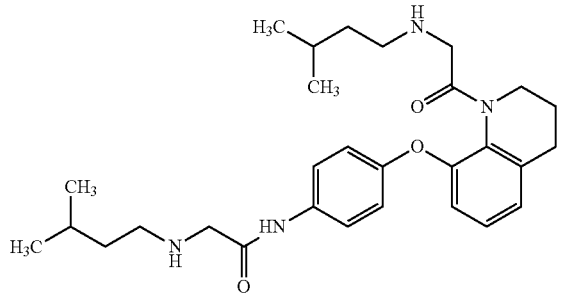 |
| 42 | 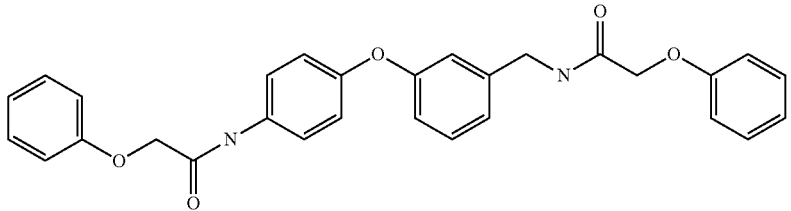 |
| 43 | 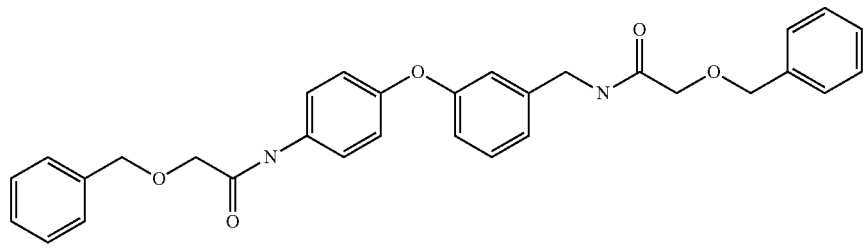 |

TABLE 1-continued

| Co. No. | Structure |
|---|---|
| 44 | (structure shown) |

Example

Virological Properties of the Compounds of the Present Invention

The compounds were tested in the anti-viral replication assay using the MT4-LTR-EGFP cells and in the ERA assay. Toxicity was measured using MT4-CMV-EGFP cells.

| Compound No | antiviral EC50 μM | Toxicity CC50 μM | ERA assay EC50 μM | ERA assay % inh |
|---|---|---|---|---|
| 1 | 1.69 | >27.7 | 92.00 | 89 |
| 4 | 5.34 | >100 | >200 | 30 |
| 5 | 3.29 | >100 | | |
| 6 | 18.57 | >100 | 182.30 | 52 |
| 7 | 57.67 | >100 | >200 | 29 |
| 8 | >100 | >100 | >200 | 3 |
| 9 | 8.64 | >32 | 79.00 | 85 |
| 10 | >32 | >32 | >100 | 48 |
| 11 | >32 | >32 | 68.85 | 64 |
| 12 | 41.34 | 54.17 | >200 | 17 |
| 16 | 54.95 | >100 | >200 | 42 |
| 20 | 3.25 | >32 | >100 | 39 |
| 21 | >34 | >100 | >200 | 9 |
| 23 | 11.19 | 34.16 | 123.00 | 92 |
| 24 | 19.46 | >100 | 78.36 | 68 |
| 29 | 1.18 | 61.62 | 177.00 | 59 |
| 30 | 0.37 | 3.85 | | |
| 31 | 0.43 | 3.41 | >100 | 13 |
| 32 | 4.17 | 19.87 | >200 | 29 |
| 33 | 5.01 | 30.16 | 196.00 | 52 |
| 34 | 1.24 | 83.19 | >200 | 41 |
| 35 | 3.28 | 23.60 | 150 | 55 |
| 36 | 1.05 | 5.87 | >200 | 9 |
| 37 | 3.92 | >32 | | |
| 39 | 1.56 | >100 | >100 | 45 |
| 40 | 0.15 | 22.39 | 40.93 | 79 |
| 42 | 3.77 | 46.48 | >200 | 37 |
| 43 | 11.76 | >32 | 83.62 | 54 |
| 44 | 2.00 | >32 | >200 | 22 |

The invention claimed is:

1. A compound selected from the group consisting of:

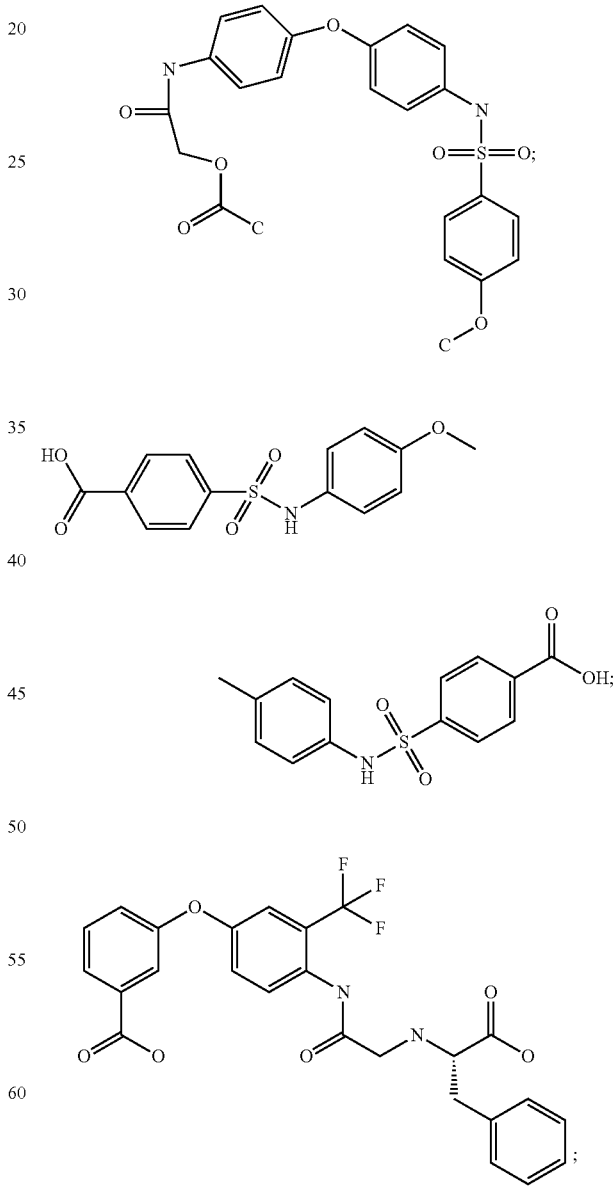

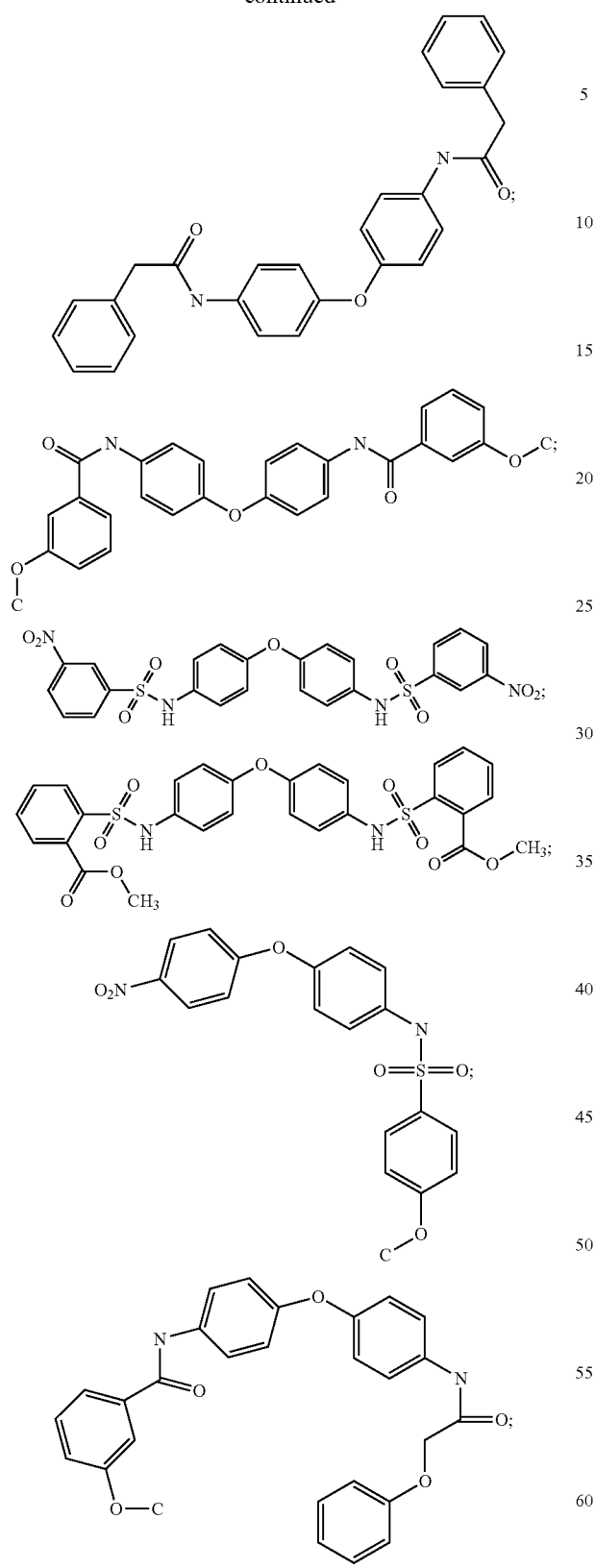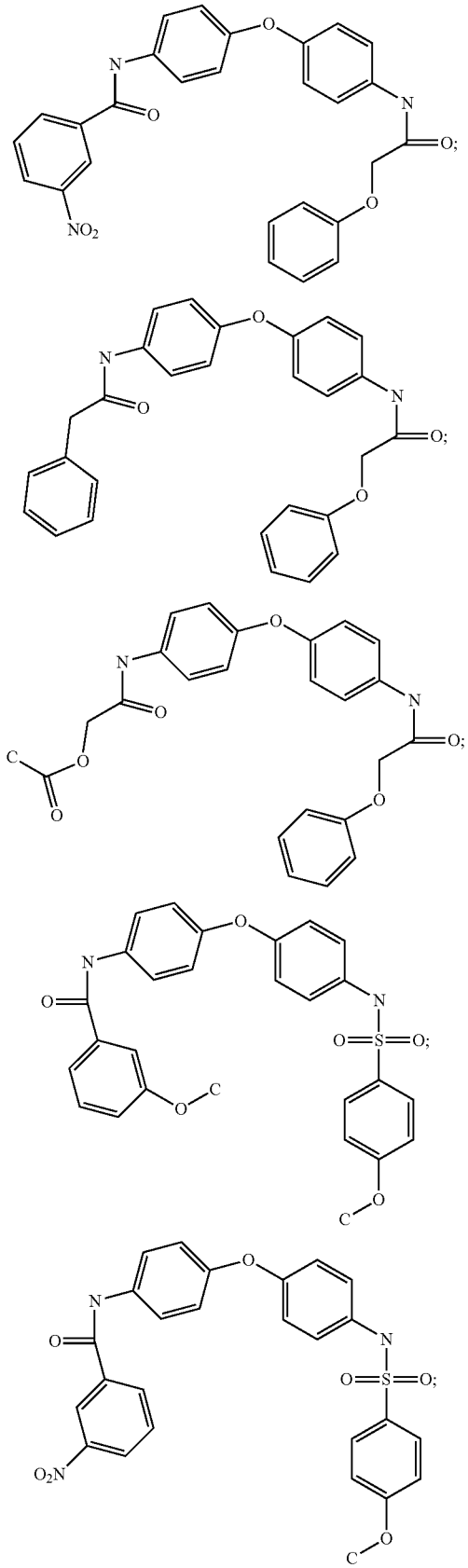

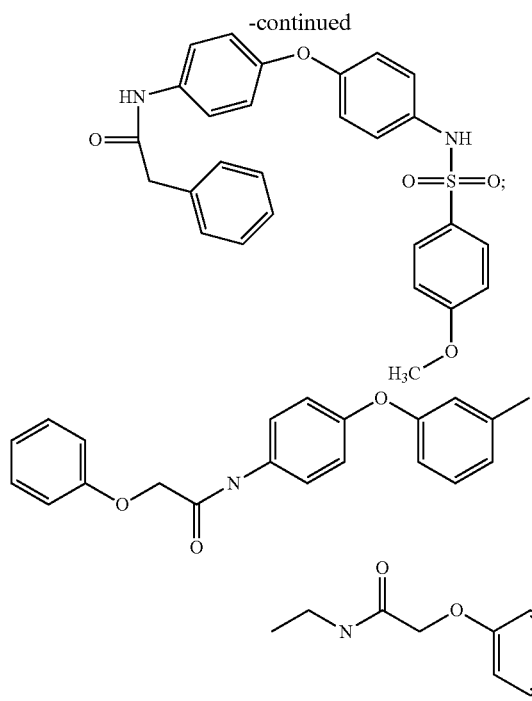
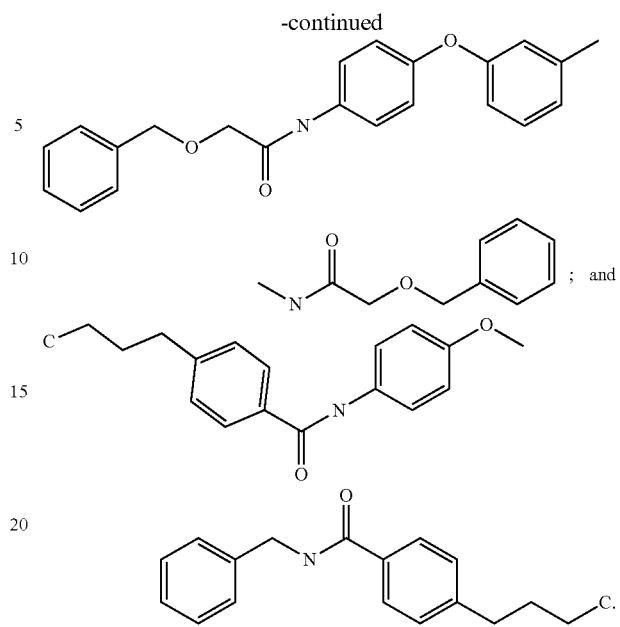
* * * * *